(12) United States Patent
Solomon et al.

(10) Patent No.: US 11,420,034 B2
(45) Date of Patent: Aug. 23, 2022

(54) CATHETER VALVES

(71) Applicant: I-V Access Technology, Inc., Los Osos, CA (US)

(72) Inventors: Clint Solomon, Morgan Hill, CA (US); Danielle Seybold, Morgan Hill, CA (US); Jacob Hentzler, Morgan Hill, CA (US)

(73) Assignee: I-V Access Technology, Inc., San Francisco, CA (US)

( * ) Notice: Subject to any disclaimer, the term of this patent is extended or adjusted under 35 U.S.C. 154(b) by 522 days.

(21) Appl. No.: 16/509,376

(22) Filed: Jul. 11, 2019

(65) Prior Publication Data

US 2019/0351210 A1 Nov. 21, 2019

Related U.S. Application Data

(63) Continuation of application No. PCT/US2018/013648, filed on Jan. 12, 2018.

(60) Provisional application No. 62/445,545, filed on Jan. 12, 2017.

(51) Int. Cl.
| | |
|---|---|
| *A61M 5/00* | (2006.01) |
| *A61M 39/06* | (2006.01) |
| *A61M 5/168* | (2006.01) |
| *A61M 25/00* | (2006.01) |

(52) U.S. Cl.
CPC ........ *A61M 39/06* (2013.01); *A61M 5/16881* (2013.01); *A61M 25/0075* (2013.01); *A61M 2039/062* (2013.01); *A61M 2039/064* (2013.01)

(58) Field of Classification Search
CPC .............. A61M 39/06; A61M 39/0613; A61M 2039/064; A61M 25/0075; A61M 5/16881; A61M 25/0606; A61M 25/0097; F16K 15/147
See application file for complete search history.

(56) References Cited

U.S. PATENT DOCUMENTS

| | | | |
|---|---|---|---|
| 4,924,923 A * | 5/1990 | Boehmer | ............... B60K 15/04 277/560 |
| 5,010,925 A | 4/1991 | Atkinson et al. | |
| 5,114,408 A | 5/1992 | Fleischhaker et al. | |
| 5,269,771 A | 12/1993 | Thomas et al. | |
| 5,484,418 A | 1/1996 | Quiachon et al. | |
| 5,533,708 A | 7/1996 | Atkinson et al. | |
| 6,024,729 A | 2/2000 | Dehdashtian et al. | |
| 6,186,997 B1 | 2/2001 | Gabbard et al. | |
| 6,261,282 B1 | 7/2001 | Jepson et al. | |
| 6,352,520 B1 | 3/2002 | Miyazaki | |
| 7,744,571 B2 * | 6/2010 | Fisher | .............. A61M 39/0606 604/167.04 |
| 7,753,338 B2 | 7/2010 | Desecki | |
| 7,914,519 B2 | 3/2011 | Moran et al. | |
| 7,947,032 B2 | 5/2011 | Harding et al. | |

(Continued)

FOREIGN PATENT DOCUMENTS

| | | |
|---|---|---|
| CN | 203263883 | 11/2013 |
| CN | 103492012 | 1/2014 |

(Continued)

*Primary Examiner* — Rebecca E Eisenberg
(74) *Attorney, Agent, or Firm* — Levine Bagade Han LLP

(57) ABSTRACT

The invention is directed to methods and devices to facilitate positioning of a catheter into a vessel and selectively controlling flow of fluids through the catheter until desired using one or more valves.

12 Claims, 10 Drawing Sheets

(56) References Cited

U.S. PATENT DOCUMENTS

| | | |
|---|---|---|
| 8,251,923 B2 | 8/2012 | Carrez et al. |
| 8,361,020 B2 | 1/2013 | Stout |
| 8,647,312 B2 | 2/2014 | Utterberg et al. |
| 8,932,259 B2 | 1/2015 | Stout et al. |
| 9,114,231 B2 | 8/2015 | Woehr et al. |
| 9,149,625 B2 | 10/2015 | Woehr et al. |
| 9,155,864 B2 | 10/2015 | Stout et al. |
| 9,427,549 B2 | 8/2016 | Woehr et al. |
| 2007/0225647 A1* | 9/2007 | Luther ............... A61M 25/0075 604/167.03 |
| 2008/0108944 A1 | 5/2008 | Woehr et al. |
| 2009/0234290 A1* | 9/2009 | Fisher ............... A61M 39/0693 604/167.04 |
| 2011/0257590 A1 | 10/2011 | Winsor et al. |
| 2012/0150118 A1 | 6/2012 | Keyser et al. |
| 2013/0204226 A1 | 8/2013 | Keyser |
| 2015/0038910 A1 | 2/2015 | Harding et al. |
| 2015/0148756 A1 | 5/2015 | Lynn |
| 2015/0265827 A1 | 9/2015 | Keyser et al. |
| 2015/0306368 A1 | 10/2015 | Lin et al. |

FOREIGN PATENT DOCUMENTS

| | | | |
|---|---|---|---|
| CN | 104415446 | 3/2015 | |
| CN | 105530989 | 4/2016 | |
| CN | 203494034 | 3/2021 | |
| WO | WO-2009114456 A1 * | 9/2009 | ........ A61M 25/0668 |
| WO | WO 2015/161294 | 10/2015 | |
| WO | WO 2018/132758 | 7/2018 | |

\* cited by examiner

CATHETER VALVES

CROSS-REFERENCE TO RELATED APPLICATIONS

This application is a continuation of International Patent Application No. PCT/US2018/013648 filed Jan. 12, 2018, which claims priority to U.S. Provisional Application No. 62/445,545 filed Jan. 12, 2017, the contents of which are incorporated herein by reference in their entirety.

FIELD OF THE INVENTION

The invention is directed to methods and devices to facilitate positioning of a catheter into a vessel and selectively controlling flow of fluids through the catheter until desired.

BACKGROUND OF THE INVENTION

The current invention relates to infusion devices, specifically to catheters where there is a need to selectively control the flow of fluid through the catheter.

Catheters allow medical practitioners to administer infusion or removal of fluids from a patient. For example, catheters can function as a conduit that allows infusion of fluids, such as normal saline solution, therapeutic substances, and/or nutritional fluids into a patient. Alternatively, catheters can withdraw fluids such as blood or other bodily fluids as required by the particular medical procedure. In those cases, where the medical practitioner intends to position the catheter into a vessel, the medical practitioner will look for a flow of blood back into the catheter ("flashback") to verify placement of the catheter opening into a vessel. The number of different catheter insertion procedures and techniques is great and may include the use of a needle, dilator, stylet, or other medical device within the catheter when placed.

Once properly positioned, the catheters hub (or medical device positioned within the catheter) can be coupled to an adapter (typically a luer fitting) to enable fluid coupling of the catheter to the source of fluids or reservoir.

However, regardless of the application, insertion of a catheter requires that the point of access remains sanitary. Often, the period between insertion of the catheter and coupling of an adaptor causes bodily fluids to escape through the catheter causing an unsanitary condition for the medical practitioner who must handle the catheter for coupling of the adapter and/or remove the medical device inserted through the catheter.

There remains a need for a catheter assembly that permits controlled fluid flow. Such a catheter assembly is described below.

BRIEF SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

The present invention includes catheter assemblies for use with a luer device. In one example a catheter assembly comprises a catheter hub having an interior cavity extending between a proximal end and a distal end; an actuating body slidably located within the interior cavity of the catheter hub and having an actuating body lumen extending therethrough, the actuating body including a shoulder surface; a valve located within the interior cavity, the valve comprising: a base having a flange extending around a perimeter of the valve, a valve lumen extending axially through the base, a valve wall extending axially in a distal direction from the base, where the valve wall surrounds the valve lumen at a distal portion of the valve, the valve wall being biased in a closed configuration such that adjacent interior surfaces of the valve wall contact to block flow through the valve lumen and prevent fluid backflow in a proximal direction through the valve lumen, wherein the adjacent interior surfaces of the valve wall are separable to assume an open configuration that allows fluid flow in a distal direction through the valve lumen; a plurality of leg extensions extending proximally from the base, the plurality of leg extensions being elastically compressible; where in the closed configuration at least a distal portion of the valve actuating body is positioned within the valve such that the actuating body lumen is in fluid communication with the valve lumen, and where the shoulder of the actuating body is adjacent to the leg extensions; wherein insertion of the luer device into the interior cavity of the catheter hub causes advancement of the actuating body in a distal direction compressing the plurality of leg extensions while moving the valve to the open configuration by causing separation of the adjacent interior surfaces of the valve wall; and wherein upon withdrawal of the luer device, the plurality of leg extensions elastically revert causing movement of the actuating body in a proximal direction such that the valve reverts to the closed configuration.

In an additional variation, each leg extension of the plurality of leg extensions are spaced from an adjacent leg extension by a gap.

The distal portion of the actuating body can comprise a tubular shape having a diameter less than a diameter of the shoulder surface.

The valves can include either a single slit opening at the distal end of the valve or a multiple or tri-slit opening at the distal end of the valve.

Variations of the device include an actuating body that comprises a plurality of alignment features to prevent rotation of the actuating body within the catheter hub.

In certain variations, the catheter hub comprises a distal portion and a proximal portion, where the distal portion and proximal portion are joined together such that the flange of the base of the valve is located between an intersection of the distal portion and proximal portion to prevent fluid flow around the valve.

In additional variations, the plurality of leg extensions are distributed circumferentially positioned about the base of the valve.

The device described herein can further comprising a tubular extension extending distally from the valve base, the tubular extension radially surrounding the valve wall, at least one flexible rib connecting an interior of the tubular extension to an exterior of the valve wall such that the flexible rib prevents prolapse of the valve wall upon proximal movement of the actuating body.

The valves used in the variations described herein can vary from a single flap valve configuration to multiple flap valve configurations.

In another variation, the devices described herein can include catheter assemblies for use with a dilator, needle, or tubular member. For example, such catheter assemblies can include a catheter hub having an interior cavity extending between a proximal end and a distal end, a tubular extension extending from the distal end and a proximal opening at the proximal end, where a catheter lumen extends from the proximal opening through the tubular extension; a valve located within the interior cavity of the hub, the valve having a closed configuration that prevents fluid flow in a proximal direction through the valve, the valve having an open configuration that allows fluid flow in a distal direction through the valve; a secondary valve located at the proximal opening of the catheter hub and having a nipple portion surrounded by a sealing portion, the nipple portion having a thickness greater than the sealing portion, an opening located through the nipple portion for passage of a dilator tubing of the dilator.

The catheter assemblies can include a secondary valve that comprises at least one slit extending through a portion of the sealing portion and ending adjacent to the nipple portion.

Variations of the secondary valve can further comprises a semicircular groove in the sealing portion that aligns with a protruding section within the interior cavity of the catheter hub, such that advancement of a male luer against the secondary valve causes the sealing portion to shear at the semicircular groove against the protruding section.

The catheter assemblies can further include a valve that comprises: a tubular valve base having an interior surface defining a cavity therein, the tubular valve base comprising a proximal end and a distal end; a flange extending around a perimeter of the tubular valve base; a valve wall extending distally within the cavity of the tubular valve base, where adjacent interior surfaces of the valve wall are spaced at the proximal end of the tubular valve base to form an opening and define a valve lumen; where at towards the distal end of the tubular valve base the adjacent interior surfaces of the valve wall are biased together such that the adjacent interior surfaces contact to form a sealed configuration obstructing the valve lumen such that valve wall prevent fluid backflow in a proximal direction through the valve lumen, wherein when adjacent interior surfaces of the valve wall separate upon insertion of the male luer causing the valve to assume an open configuration that allows fluid flow in a distal direction through the valve lumen.

In additional variations, the valve can further include at least one flexible rib extending from the interior surface of the tubular base and coupled to a portion of the valve wall such that the flexible rib prevents prolapse of the at least two valve walls upon removal of the male luer from within the valve lumen.

In an additional variation, the present devices can include a valve for use with a catheter hub and a luer connector, the catheter hub having an interior cavity extending between a proximal end and a distal end, the luer connector comprising a male luer fitting. For example such a valve can include a tubular base having an interior surface defining a cavity therein, the tubular base comprising a proximal end and a distal end; a flange extending around a perimeter of the tubular base, a valve wall extending distally within the cavity of the base, where adjacent interior surfaces of the valve wall are spaced at the proximal end of the tubular base to form an opening and define a valve lumen; where at towards the distal end of the tubular base the adjacent interior surfaces of the valve wall are biased together such that the adjacent interior surfaces contact to form a sealed configuration obstructing the valve lumen such that valve wall prevent fluid backflow in a proximal direction through the valve lumen, wherein when adjacent interior surfaces of the valve wall separate upon insertion of the male luer causing the valve to assume an open configuration that allows fluid flow in a distal direction through the valve lumen; a plurality of flexible ribs extending from the interior surface of the tubular base and coupled to a portion of the valve wall such that the plurality of flexible ribs prevent prolapse of the valve wall upon removal of the male luer from within the valve lumen.

BRIEF DESCRIPTION OF THE DRAWINGS

Each of the following figures diagrammatically illustrates aspects and variation to better understand the invention. Variation of the invention from the aspects shown in the figures is contemplated.

DETAILED DESCRIPTION

One purpose of a valve described herein is to function as a blood block valve in a catheter application (e.g., peripheral IV catheters). This involves placement of the valve in the hub (or otherwise in fluid communication with a flow path) of a catheter to block blood flow from a patient's vein during initial venipuncture lower the risk of blood exposure from the hub and contamination of the site. Such an improvement allows a medical professional or caregiver to preserve a clean access site to avoid the transfer of blood borne pathogens. The devices described herein can also be used in in check valves, needleless injection ports, and backflow prevention devices as well as non-medical fluid applications.

Figure 1A:
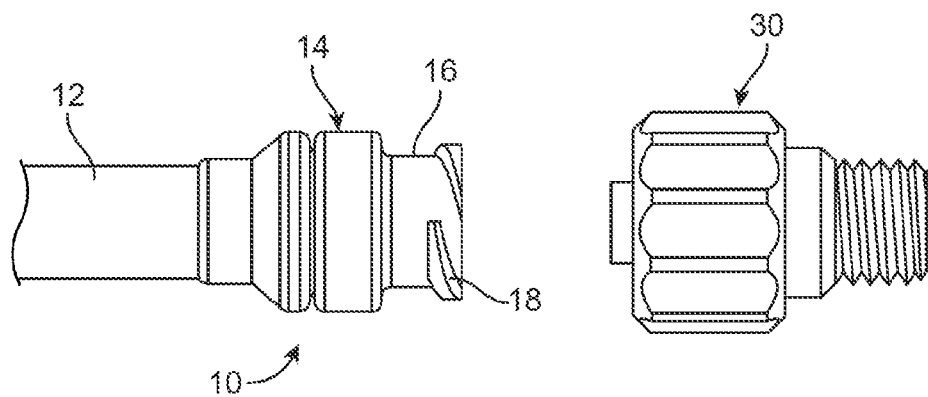
FIGS. 1A and 1B illustrate an example of a catheter having an internal valve that retains fluid in the catheter until a second device engages the catheter and opens the valve.
Figure 1B:
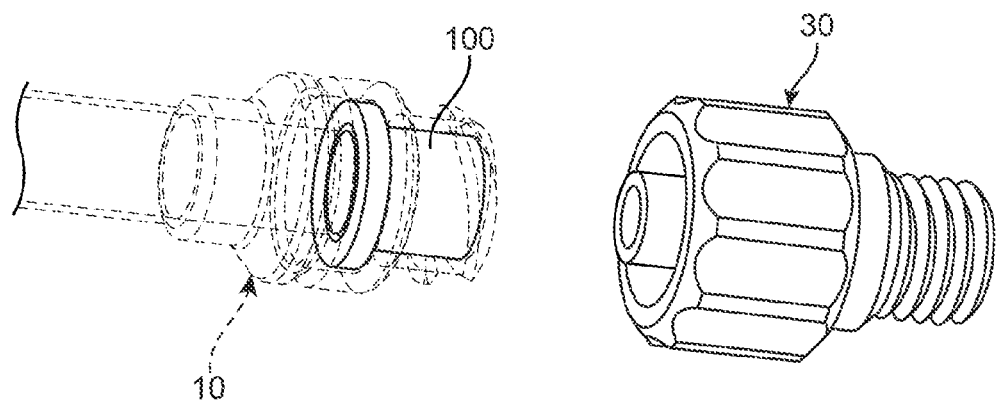

The present valve designs prevent blood from flowing freely through a catheter 10 (or other medical device) into an open environment where there is a risk of blood borne pathogens (or other substances) contacting the caregiver. FIG. 1A illustrates an example of a catheter having an internal valve that reduces this risk by retaining the blood in the catheter 10 until a second device such as a fitting 30 (e.g., a luer fitting as shown) or a second medical device (e.g., a dilator not shown) engages the catheter 10 and opens the valve. The catheter 10 typically includes a catheter tubing or extrusion 12 extending from a hub 14. The valves are typically positioned within an interior cavity of the hub 14 (as shown in FIG. 1B) in a fluid flow path that extends from the hub 14 through a distal end of the catheter extrusion 12. The hub 14 can be a unitary structure or can be a multi-structure component. In certain variations, a proximal end of the hub 16 includes a thread 18 that allows for coupling of the second device. Furthermore, the interior of the hub 14 can include a female luer taper or cavity that allows assists in creating a fluid seal with a male tapered fitting. In a normal position, the valve prevents fluid flow through the catheter 10 until insertion of the fitting 30 (or second medical device) into the catheter hub 14 causes the valve to assume an open configuration and restore flow directly through the fitting 30 (or second medical device) and through the catheter 10. The open configuration can be caused directly by the fitting (or second medical device) acting upon the valve. Alternatively, the open configuration can be caused by movement of an actuating component that opens the valve as described herein.

Figure 2A:
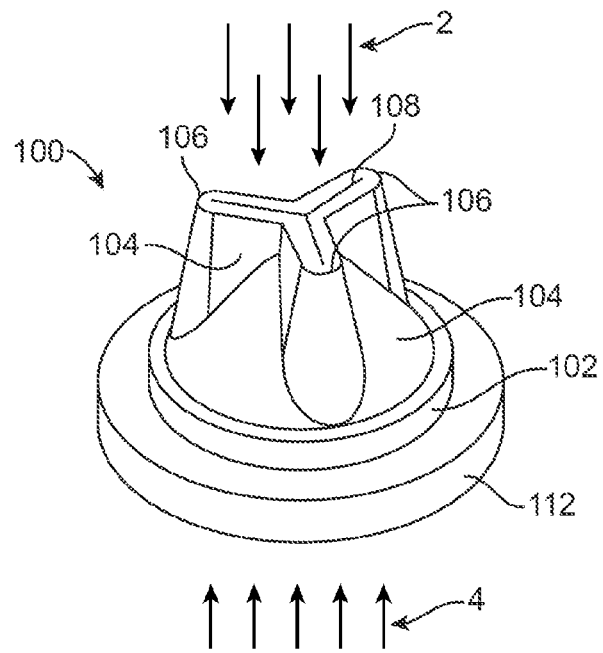
FIGS. 2A to 2C illustrate variations of valves for use with catheters to control fluid flow through the catheter.

FIG. 2A illustrates a first variation of a valve 100. As shown, the valve 100 includes a base 102 having a valve wall 104 extending in an axially distal direction from the base 102 where the valve wall 104 surrounds a valve lumen (not shown but interior to the valve 100). The valve base 102 can include one or more flanges 112 that assist in securing the valve 100 within the catheter hub or assist in a sealing function of the valve. The flange 112 can be positioned about the body 102 either continuously about a perimeter of the base 102 or intermittently about the base (not shown).

The valve wall 104 is typically set or biased in a closed configuration towards a distal end of the valve such that a plurality of interior surfaces of the valve wall 104 contact or close together to block flow through the valve lumen. The configuration is commonly referred to as a duck bill configuration such that in the closed configuration the structure of the valve wall 104 prevents fluid backflow 2 due in part to the pressure exerted on the exterior surface of the valve wall 104 unless there is a force exerted on the interior of the valve walls moving them into an open configuration. The valve lips or flaps 106 seal when pressurized from backflow, where slits 108 in a distal end/surface of the valve 100 allow the valve to open when opened by the actuator, when forward flow 4 is present, and/or when a second medical device is positioned through the valve.

Figure 2B:
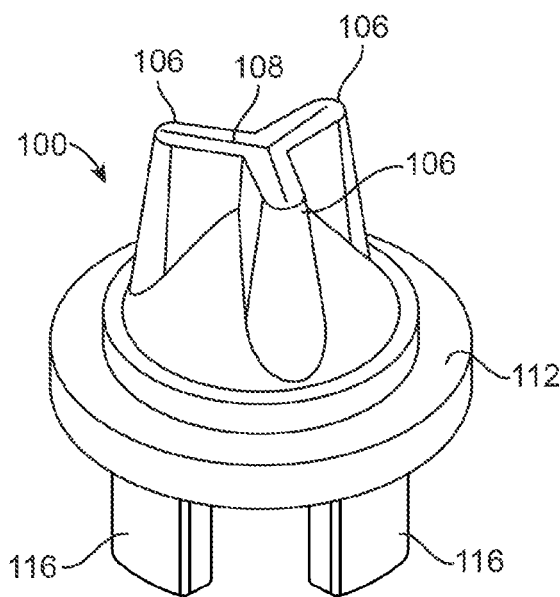
Figure 2C:
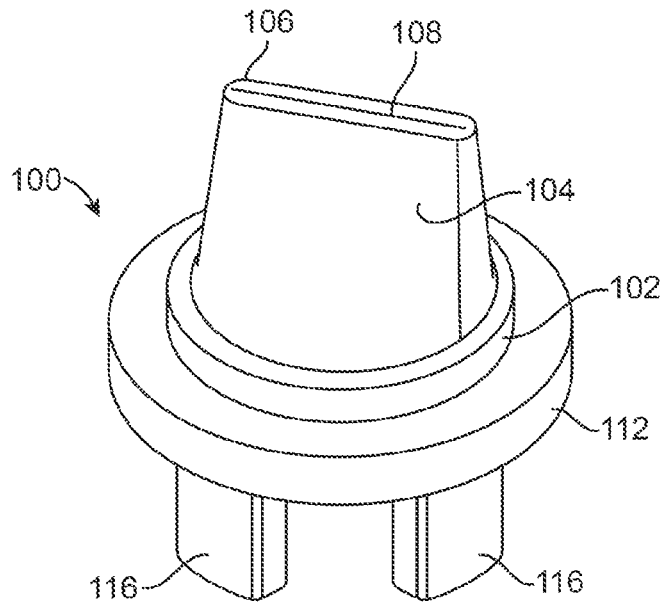

As illustrated, variations of the device include a valve wall 104 that is set to form a single flap 106 (see FIG. 2C) or a multiple flap 106 configuration (see FIG. 2B). Typically, the valve 100 is formed from a thin walled elastomeric material where the flaps or lips are formed by slits on its distal end surface of the valve.

As disclosed below, variations of the valve designs can require an actuator to open the valve when engaged with a male luer. In such a case, the luer, slip or lock, pushes an actuator to open the valve, allowing unrestricted flow directly through the luer. The valve is seated and fixtured at its base with a flat, gasket-like sealing element. FIG. 2B illustrates a variation of a valve 100 having a construction similar to that shown in FIG. 2A but with the addition of one or more elastic or resilient leg extensions 116 that can extend proximally from the base (or the flange) 112. The leg extensions 116 can be elastically compressible such that they increase a force to displace an actuator (or connector/second medical device) out of the valve when the user intends to seal the valve. In the illustration shown in FIG. 2B, the leg extensions 116 are positioned below the sealing surface (or flange 112) of the valve 100 to act as a spring when an actuator is pushed into the valve by the luer fitting.

Figure 3:
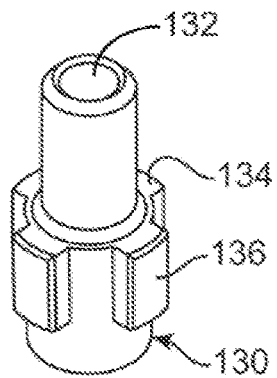
FIG. 3 illustrate an example of an actuating body that is positioned within a catheter hub and that moves a valve into an open configuration.

FIG. 3 illustrates an example of an actuator or actuating body 130 that can be positioned within an interior cavity of a catheter hub. The actuating body 130 can include an actuating body lumen 132 that allows fluid to flow through the actuator body 130. Alternatively, the actuator body 130 can be designed such that it does not occlude a catheter hub when placed therein but can still open the valve. This variation of the actuating body 130 also includes a plurality of shoulder surfaces 134 that, as discussed, below engage a portion of the valve. The shoulder surfaces 134 can also be combined with alignment features 136 that prevent rotation of the actuator body 130 when within a catheter hub. The alignment features 136 keep the actuator in its designated location and inhibit actuator rotation in three degrees.

Figure 4A:
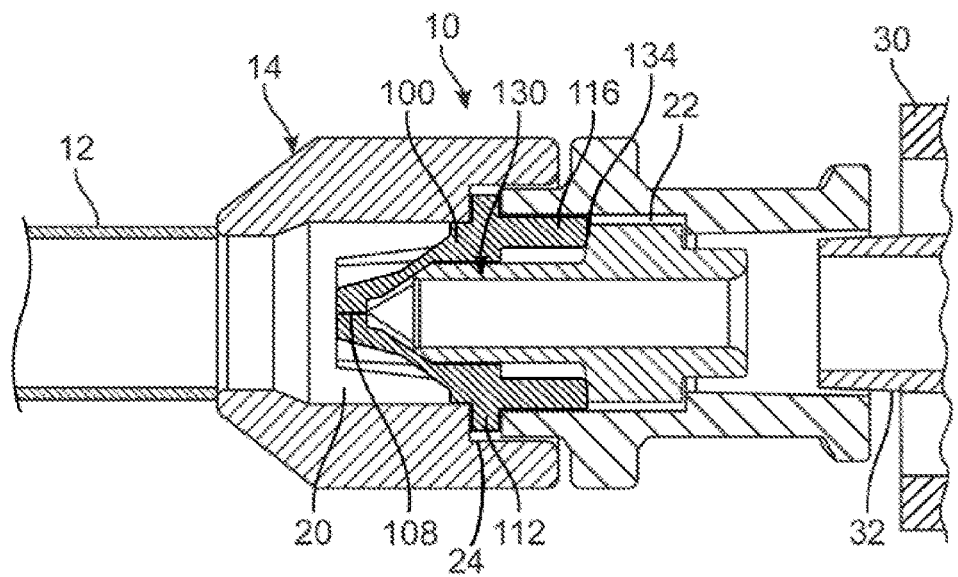
FIGS. 4A and 4B show partial cross sectional views of a catheter having a valve and actuator body located within a cavity of a catheter hub.

FIG. 4A a cross sectional view of an example of a catheter 10 having a valve 100 and actuator body 130 located within a cavity 20 of a catheter hub 14. As illustrated, the actuator body includes a should surface 134 that can be positioned adjacent to a leg 116 of a valve 100. As shown, the valve 100 is maintained in place within the catheter hub 14 as a sealing ring or flange 112 is positioned within a groove 24 of the catheter hub. Alternatively, the sealing ring or flange 112 can be clamped between two adjacently joined components of the catheter hub. The illustrated example also shows an optional feature where the actuator body 130 includes anti-rotational surfaces or features 136 that are positioned within a slot 22 of the catheter hub 14. The valve 100 shown in FIG. 4A is in a closed configuration that prevents fluid backflow as described above.

Figure 4B:
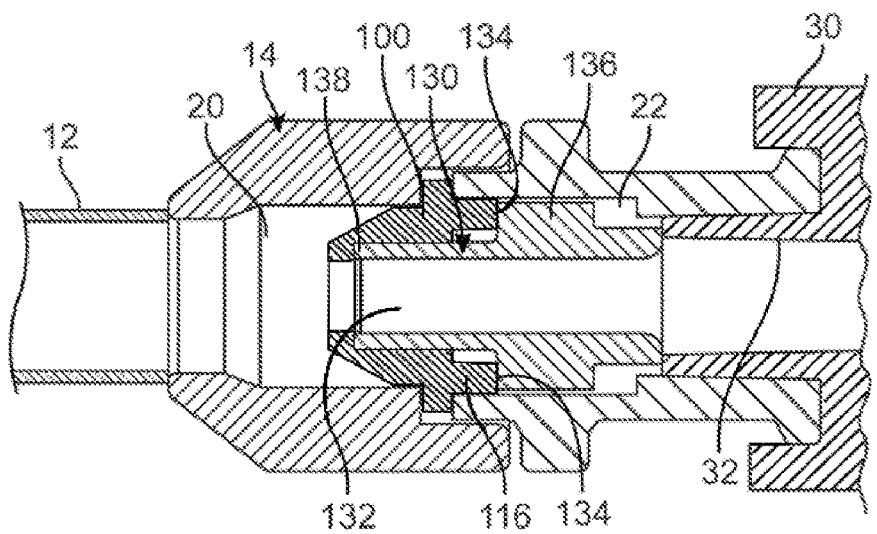

FIG. 4A illustrates a fitting 30 having a male luer 32 being inserted into a proximal end of the catheter hub 14. FIG. 4B illustrates the state where the male luer 32 advances the actuator body 130 such that a distal end 138 of the actuator body 130 separates the slit 108 of the valve to move the valve into an open configuration. As shown in FIG. 4B, the shoulder surface 134 of the actuator body 130 compresses legs 116 of the valve 100. The compression of the legs 116 is maintained by the force applied by the connector 30/male luer 32 on the proximal end of the actuator body 130. This state allows fluid flow through the connector 30, actuator body lumen 132, cavity 20, and ultimately through the catheter extrusion 12. As long as the actuator body 130 maintains the valve 100 in an open configuration, fluid flow can occur in a proximal or distal direction. At the appropriate time, removal of the connector 30 from the catheter hub 14 withdraws the male luer 32 from the catheter hub 14, which removes the force applied to the actuator body 130. This causes the resilient legs 116 to drive the actuator body 130 in a proximal direction causing the valve to revert to a closed configuration, as illustrated by FIG. 4A.

Figure 5A:
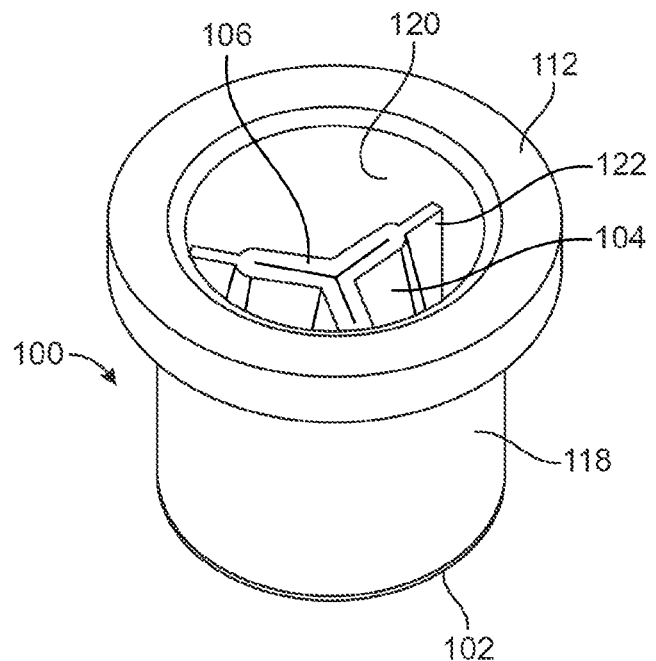
FIGS. 5A and 5B illustrate variations of a valve having features to prevent prolapse or inversion of the valve flaps upon removal of a male luer fitting or actuator body.
Figure 5B:
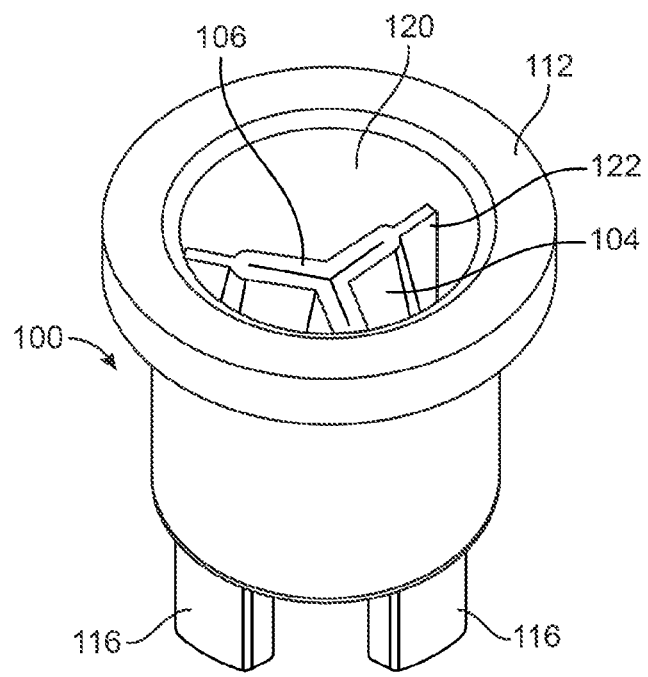

FIGS. 5A and 5B illustrate variations of a valve 100 having features to prevent prolapse or inversion of the valve flaps 106 upon removal of a male luer fitting or actuator body. FIG. 5A is a variation of a valve 100 that eliminates the need for an actuator body where a male luer (or other medical device) functions to open the valve. FIG. 5B illustrates a valve with leg extensions 116 for use with an actuator body as described above.

As illustrated, the valve 100 includes a tubular base or extension 118 extending from a base or proximal end 102 of the valve 100. The tubular extension 118 includes an interior surface 120 defining a cavity therein. The tubular extension comprises a proximal end and a distal end, with a flange 112 located a distal end about an opening of the cavity. As discussed above, the valve 100 includes a valve wall 104 extending in a distal direction to form flaps 106. However, in this variation, the flaps 106 are supported by one or more flexible ribs 122 extending from the interior surface 120 of the tubular extension 118 and coupled to a portion of the valve wall 104 or flaps 106 such that the plurality of flexible ribs 122 prevent prolapse or inversion (in a proximal direction) of the valve wall upon removal of the male luer (or actuator) from within the valve lumen. The ribs 122 can also assist in maintaining the flaps 106 in a centered position within the cavity of the tubular base 118 or maintaining the flaps 106 in a closed configuration.

The ribs act can also act as tension members that overcome the drag forces present on the interior of the valve wall during the removal of the male luer or other device. Variations of the device include ribs that sufficiently thin or are configured to buckle in compression, thus reducing the transmission of compressive loads to the valve lips from the exterior base wall when fit into a catheter hub.

Figure 6:
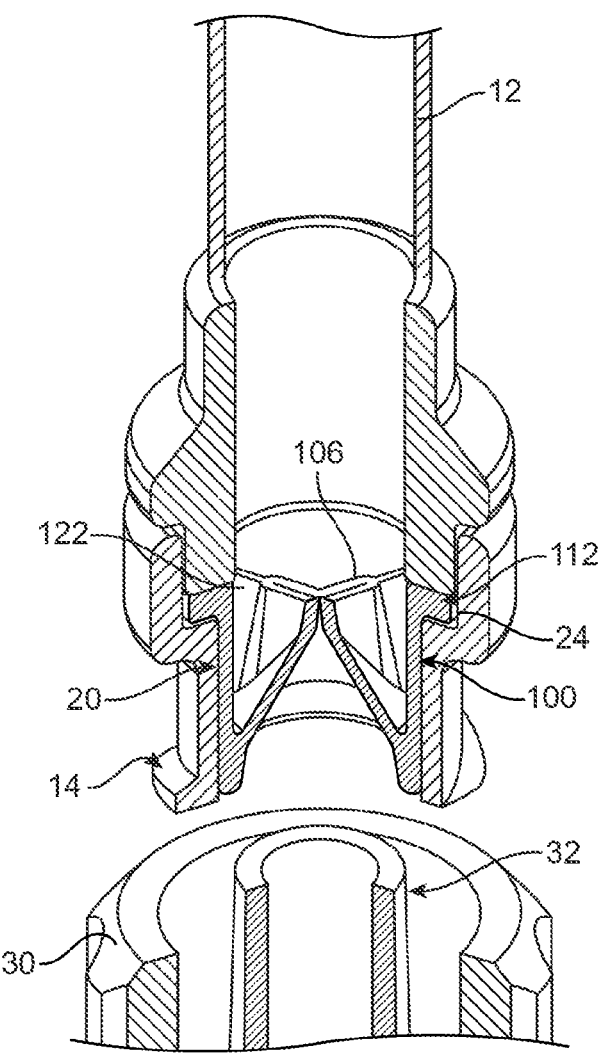
FIG. 6 illustrates a valve as described herein that does not require an actuator body to move between an open configuration and a closed configuration.

FIG. 6 shows a variation of a valve 100 (such as described herein) positioned within a cavity 20 of a catheter hub 14 that does not require an actuator body to move the valve 100 to an open configuration. As illustrated, the valve 100 includes a valve wall that terminates in a series of flaps or lips 106 that are supported by rib members 122 as described above. The valve 100 includes a closed configuration, as shown. When a medical practitioner inserts a second device such a connector 30 with a male luer 32, the luer 32 advances against the valve wall and separates the valve walls to assume an open configuration that allows fluid flow in a distal direction through the valve lumen. Alternatively, a dilator or other device can be positioned within the valve 100.

The variation shown in FIG. 6 can be configured to accommodate male luers of varying lengths without influencing flow characteristics, seal, or lock strength. In certain variations, the valve 100 itself can form a seal around the male luer instead of relying on a standard rigid female luer taper geometry on an interior of the catheter hub. Alternatively, the valve can supplement the standard rigid female luer taper geometry. In any case, once the luer is removed, the valve 100 naturally reverts to the closed position where the pressure of the backflowing fluid acts normal to the lips 106 to assist in maintaining a seal.

Figure 7A:
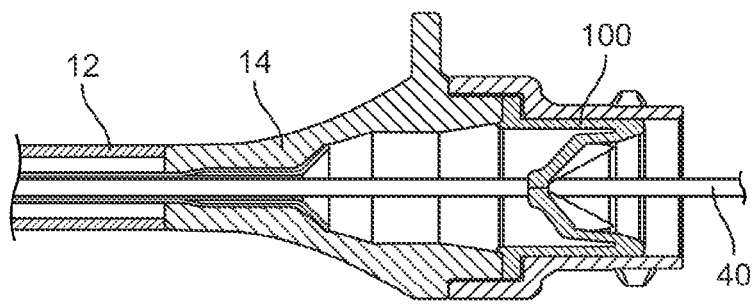
FIGS. 7A to 7C illustrate partial cross sectional views of a conventional dilator that is advanced through a valve and catheter hub assembly as described herein.
Figure 7B:
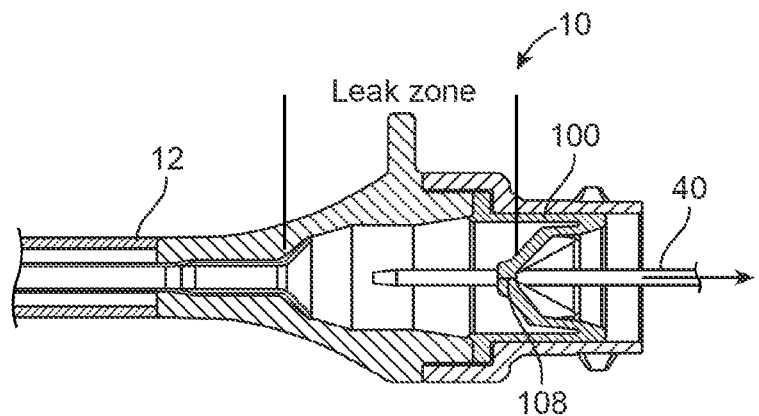
Figure 7C:
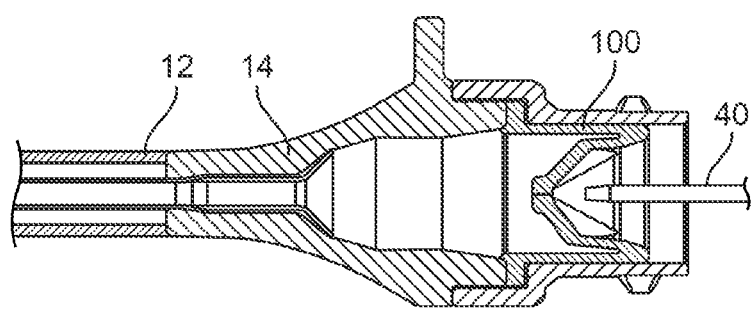

FIGS. 7A to 7C illustrate partial cross sectional views of a conventional dilator 40 that is advanced through a valve 100 and catheter hub 14 assembly as described herein. Although a dilator is shown in the following description and figures, a needle can be used in place of a dilator.

As shown in FIG. 7A, a dilator 40 extends from the proximal end of the catheter hub 14, through the valve 100, and into the catheter tubing 12. FIG. 7B illustrates removal of the dilator 40 from the catheter tubing 12. However, in some variations of the device, a leak zone might develop in the region between the opening or slit 108 of the valve 100 and the end of the catheter tubing 12. In most cases, the valve 100 assumes a closed configuration (as shown in FIG. 7C) and fully seals the catheter 10. It should be noted that any variation of the valves discussed herein can be used in or adjacent to the catheter hub 14.

Figure 7D:
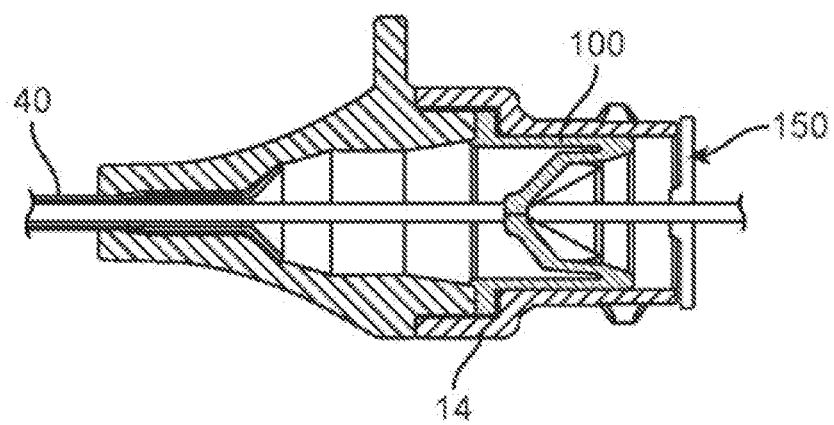
FIGS. 7D to 7F illustrate a variation of a device having a secondary valve located on or in a proximal end of a catheter hub.
Figure 7E:
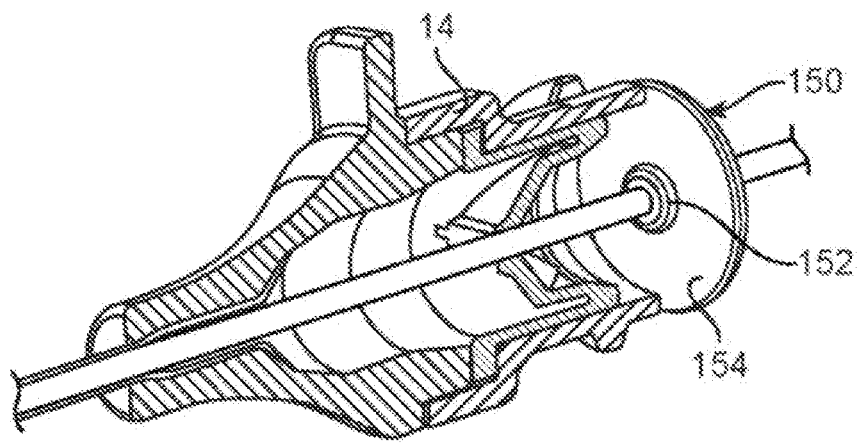
Figure 7F:
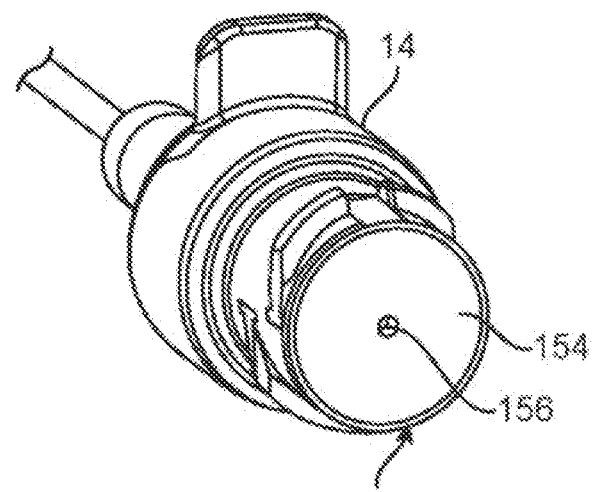

FIGS. 7D to 7F illustrate an additional variation of a catheter assembly, where the catheter tubing is omitted for purposes of illustration of a secondary valve 150 used in addition to a primary valve 100. The secondary valve 150 works in tandem with the primary valve 100 to seal the system and prevent fluid arising from the leak zone or fluid on the dilator/needle from contaminating or contacting a caregiver. The secondary valve 150 can be located at the proximal opening (or within the proximal opening) of the catheter hub 14. The secondary valve 150 includes a nipple portion 152 surrounded by a sealing portion 154, the nipple portion 152 having a thickness greater than the sealing portion 154. In addition, the nipple portion 152 includes an opening 156 located through the nipple portion for passage of a dilator tubing or secondary device.

Figure 7G:
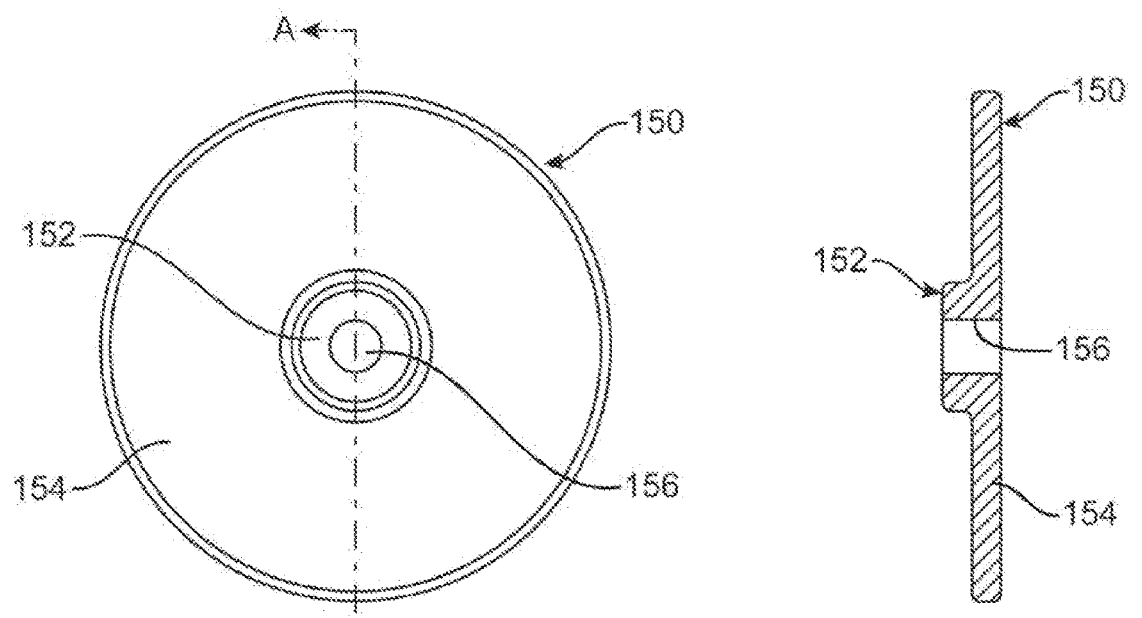
FIG. 7G shows an example of a secondary valve.
Figure 7G:
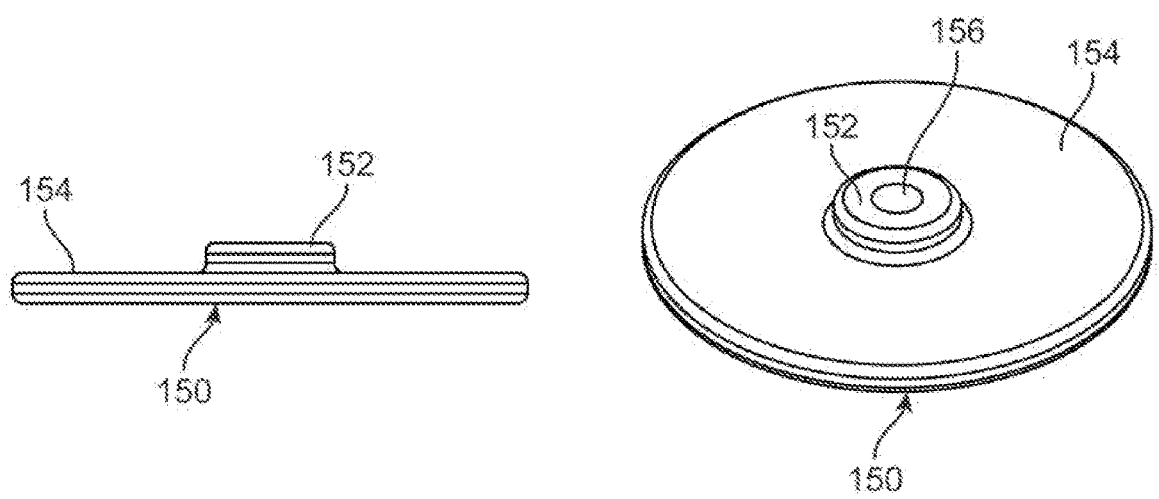

As shown in FIG. 7G, the secondary valve 150 provides an elastic membrane with an opening through the center to allow for dilator/needle insertion/withdrawal. Typically, the opening 156 is sized to be smaller than the dilator OD to form a seal therebetween. The nipple portion 152 of the secondary valve 150 prevents leaks when the dilator is extracted, where the added thickness of the nipple section 152 allows the dilator/needle to be removed either in alignment/concentrically or at an angle or non-concentrically. This thicker section strengthens the grip around the dilator so that, when stressed, the thinner sealing section 154 stretches instead of the opening 156 itself. Although variations of a secondary valve do not require a nipple section, omission of the nipple section 152 can result in a stretching of the opening given dilator misalignment. The secondary valve 150 can be bonded or over molded onto the proximal end of the catheter hub.

In certain variations, a lubricant or lubricious coating is applied on the outer surface of the valve to prevent the valve from sticking to the luer, over-stretching, and not opening fully. In certain variations the nipple section points distally to minimize the ID of the male luer from snagging on the nipple section. In additional variations the nipple may extend proximally or in both proximal and distal directions. An additional benefit of the secondary valve is that it wipes the outer surface of the dilator to prevent further risk of contamination of the injection site.

Figure 8A:
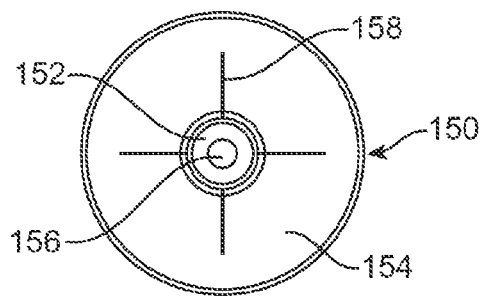
FIGS. 8A-8C illustrate additional variations of secondary valve designs.
Figure 8B:
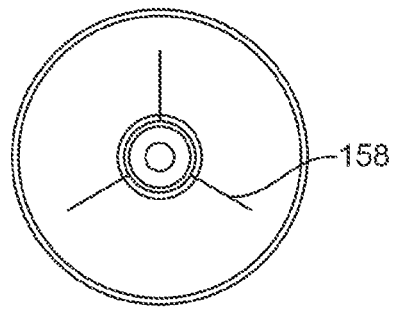
Figure 8C:
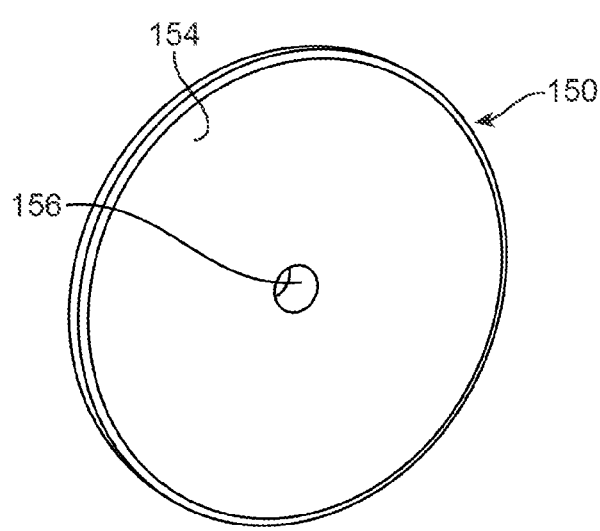
Figure 8C:
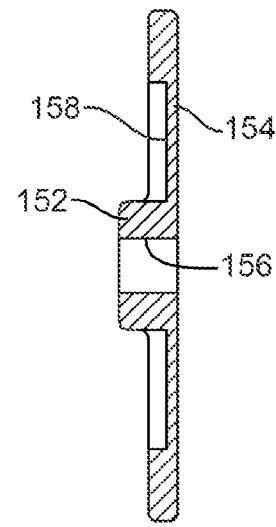

FIGS. 8A-8C illustrate additional variations of the secondary valve 150 design. As shown in FIGS. 8A and 8B, the thin sealing section 154 of the valve 150 can include a partial slit 158 in a crosswise, tri-slit, or any type of configuration such that it does not fully penetrate the valve. This would serve to weaken the valve so that it tears when engaged with a luer, thus leaving short flaps that do not interfere with the primary valve. FIG. 8C illustrates a rear isometric view of the secondary valve 150 and a cross sectional side view of the secondary valve 150 with the slit 158 only partially extending through the valve. In alternate variations, the slit can be a full length slit. Once the dilator has been extracted, the secondary valve has served its purpose, and no longer needs to function as a sealing device. When a male luer engages with the valve, it stretches until the hole opens wide enough to fit around the luer body, thus plastically deforming the valve. This allows for full flow through the male luer and does not interfere with the function of the primary valve.

Figure 9A:
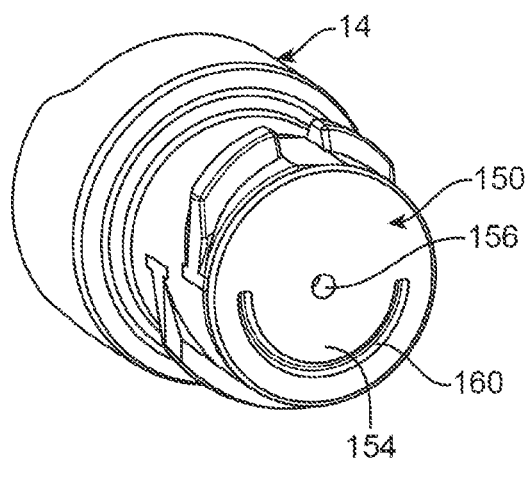
FIGS. 9A to 9D illustrate an additional variation of a secondary valve having a groove or slit that shears upon insertion of a male luer, where the shearing creates a flap that does not interfere with the operation of a main internal valve.
Figure 9B:
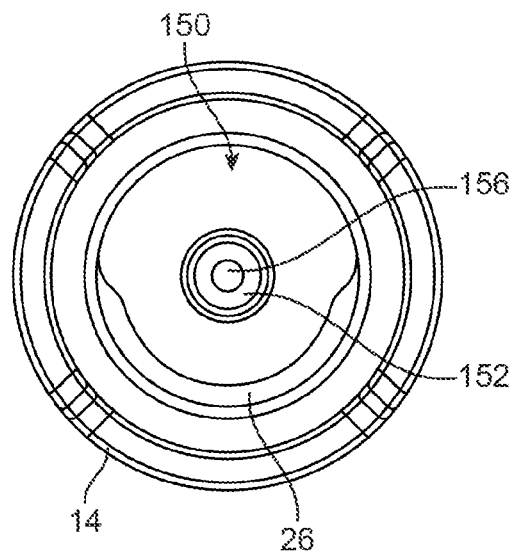
Figure 9C:
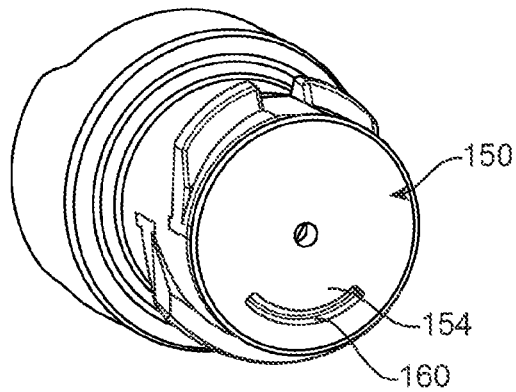
Figure 9D:
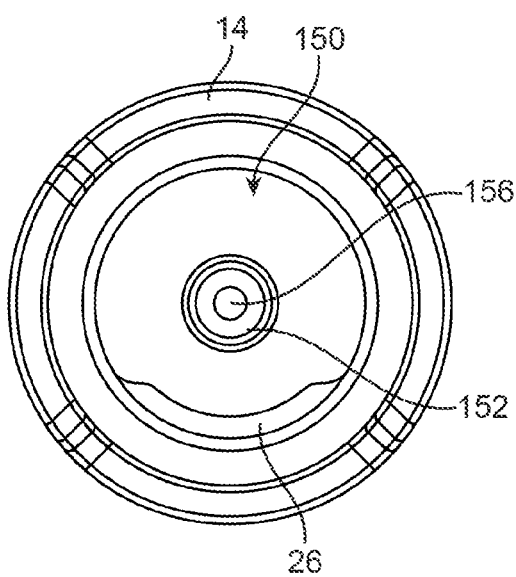

FIGS. 9A to 9D illustrate an additional variation of a secondary valve 150 coupled to a catheter hub 14. In this variation, the secondary valve 150 includes a semi-circle groove or partial slit 160 in the thinner sealing section 154. FIGS. 9A and 9C illustrate a rear view of the secondary valve 150 and catheter hub 14 while FIGS. 9B and 9D show a view through a cavity of the hub 14 that illustrates the secondary valve 150. As shown in FIGS. 9B and 9D, the groove/slit 160 aligns with a protruding section 26 on or in the catheter hub 14. When the male luer (not shown) is inserted into the hub 14 it engages the secondary valve 150. The raised shoulder 26 of the hub 14 is configured to form a tight fit with the luer to cause a shearing of the secondary valve 150 along the groove 160. This shearing causes formation of a flap in the sealing section 154 that does not interfere with the primary valve (not shown but discussed above.) As shown in FIGS. 9A and 9C, the groove 160 can be a half circle groove, a quarter circle groove or can have any length depending on the application.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

The invention claimed is:

1. A catheter assembly for use with a luer device, the catheter assembly comprising:
    a catheter hub having an interior cavity extending between a proximal end and a distal end;
    an actuating body slidably located within the interior cavity of the catheter hub and having an actuating body lumen extending therethrough, the actuating body including a shoulder surface;
    a valve located within the interior cavity, the valve comprising:
        a base having a flange extending around a perimeter of the valve,
        a valve lumen extending axially through the base,
        a valve wall extending axially in a distal direction from the base, where the valve wall surrounds the valve lumen at a distal portion of the valve, the valve wall being biased in a closed configuration such that an adjacent interior surface of the valve wall contacts to block flow through the valve lumen and prevent fluid backflow in a proximal direction through the valve lumen, wherein the adjacent interior surface of the valve wall are separable to assume an open configuration that allows fluid flow in a distal direction through the valve lumen;
        a plurality of leg extensions extending proximally from the base, the plurality of leg extensions being elastically compressible;
    where in the closed configuration at least a distal portion of the actuating body is positioned within the valve such that the actuating body lumen is in fluid communication with the valve lumen, and where the shoulder surface of the actuating body is adjacent to the plurality of leg extensions;
    wherein insertion of the luer device into the interior cavity of the catheter hub causes advancement of the actuating body in a distal direction compressing the plurality of leg extensions while moving the valve to the open configuration by causing separation of the adjacent interior surface of the valve wall; and
    wherein upon withdrawal of the luer device, the plurality of leg extensions elastically revert causing movement of the actuating body in a proximal direction such that the valve reverts to the closed configuration.

2. The catheter assembly of claim 1, where each leg extension of the plurality of leg extensions are spaced from an adjacent leg extension by a gap.

3. The catheter assembly of claim 1, where a distal portion of the actuating body comprises a tubular shape having a diameter less than a diameter of the shoulder surface.

4. The catheter assembly of claim 1, where the valve comprises a single slit opening at a distal end of the valve.

5. The catheter assembly of claim 1, where the valve comprises a tri-slit opening at a distal end of the valve.

6. The catheter assembly of claim 1, where the actuating body comprises a plurality of alignment features to prevent rotation of the actuating body within the catheter hub.

7. The catheter assembly of claim 1, where the flange of the base is positioned within a groove in the interior cavity of the catheter hub to prevent fluid flow around the valve.

8. The catheter assembly of claim 1, where the catheter hub comprises a distal portion and a proximal portion, where the distal portion of the catheter hub and the proximal portion of the catheter hub are joined together such that the flange of the base of the valve is located between an intersection of the distal portion of the catheter hub and the proximal portion of the catheter hub to prevent fluid flow around the valve.

9. The catheter assembly of claim 1, the plurality of leg extensions is distributed circumferentially positioned about the base of the valve.

10. The catheter assembly of claim 1, where the valve further comprises a tubular extension extending distally from the base of the valve, the tubular extension radially surrounding the valve wall, at least one flexible rib connecting an interior of the tubular extension to an exterior of the valve wall such that the at least one flexible rib prevents prolapse of the valve wall upon proximal movement of the actuating body.

11. The catheter assembly of claim 1, where the valve wall forms a single flap valve configuration.

12. The catheter assembly of claim 1, where the valve wall forms a multiple flap valve configuration.

* * * * *